(12) United States Patent
Ovil et al.

(10) Patent No.: US 8,784,292 B2
(45) Date of Patent: Jul. 22, 2014

(54) DOUBLE BALLOON PUMP CARDIAC ASSIST DEVICE AND RELATED METHOD OF USE

(76) Inventors: Yoel Ovil, Herzliya (IL); Yotam Ovil, Herzliya (IL); Ace Ovil, Charleston, WV (US)

( * ) Notice: Subject to any disclaimer, the term of this patent is extended or adjusted under 35 U.S.C. 154(b) by 0 days.

(21) Appl. No.: 13/550,555

(22) Filed: Jul. 16, 2012

(65) Prior Publication Data
US 2013/0184515 A1     Jul. 18, 2013

Related U.S. Application Data

(63) Continuation-in-part of application No. 11/788,887, filed on Apr. 23, 2007, now Pat. No. 8,221,303.

(60) Provisional application No. 60/794,091, filed on Apr. 24, 2006.

(51) Int. Cl.
    *A61M 1/12*          (2006.01)

(52) U.S. Cl.
    USPC .............................................. 600/18; 600/16

(58) Field of Classification Search
    USPC .......................................................... 600/18
    See application file for complete search history.

(56) References Cited

U.S. PATENT DOCUMENTS

| | | | | |
|---|---|---|---|---|
| 4,552,127 A | * | 11/1985 | Schiff | 600/18 |
| 4,692,148 A | * | 9/1987 | Kantrowitz et al. | 600/509 |
| 4,771,765 A | * | 9/1988 | Choy et al. | 600/18 |

* cited by examiner

*Primary Examiner* — Michael Kahelin
(74) *Attorney, Agent, or Firm* — Onofrio Law; Dara L. Onofrio, Esq.

(57) ABSTRACT

A system and method for cardiac assist of a heart in a beating stage comprising a double balloon catheter having a proximal end and a distal end, the catheter having at least one lumen; an inflatable intra-ventricular balloon mounted on the catheter near the distal end of the catheter, the balloon having a lumen in fluid communication with the lumen of the catheter and being configured for inflation in a ventricle; and an intra-aortic balloon mounted on the catheter proximally to the intra-ventricular balloon; a control unit comprising a bidirectional pump; a fluid reservoir; and a processor configured to activate the pump; wherein the proximal end of the catheter is configured for attachment to the control unit to form a fluid conduction system in which fluid is configured to be pumped by the pump between the fluid reservoir and the intra-ventricular balloon and the intra-aortic balloon; and systolic augmentation comprising a new pressure wave which is generated when said balloon is inflated at the end of the slow ejection phase of the beating heart, such that any residual volume of blood left in said ventricle is displaced.

31 Claims, 10 Drawing Sheets

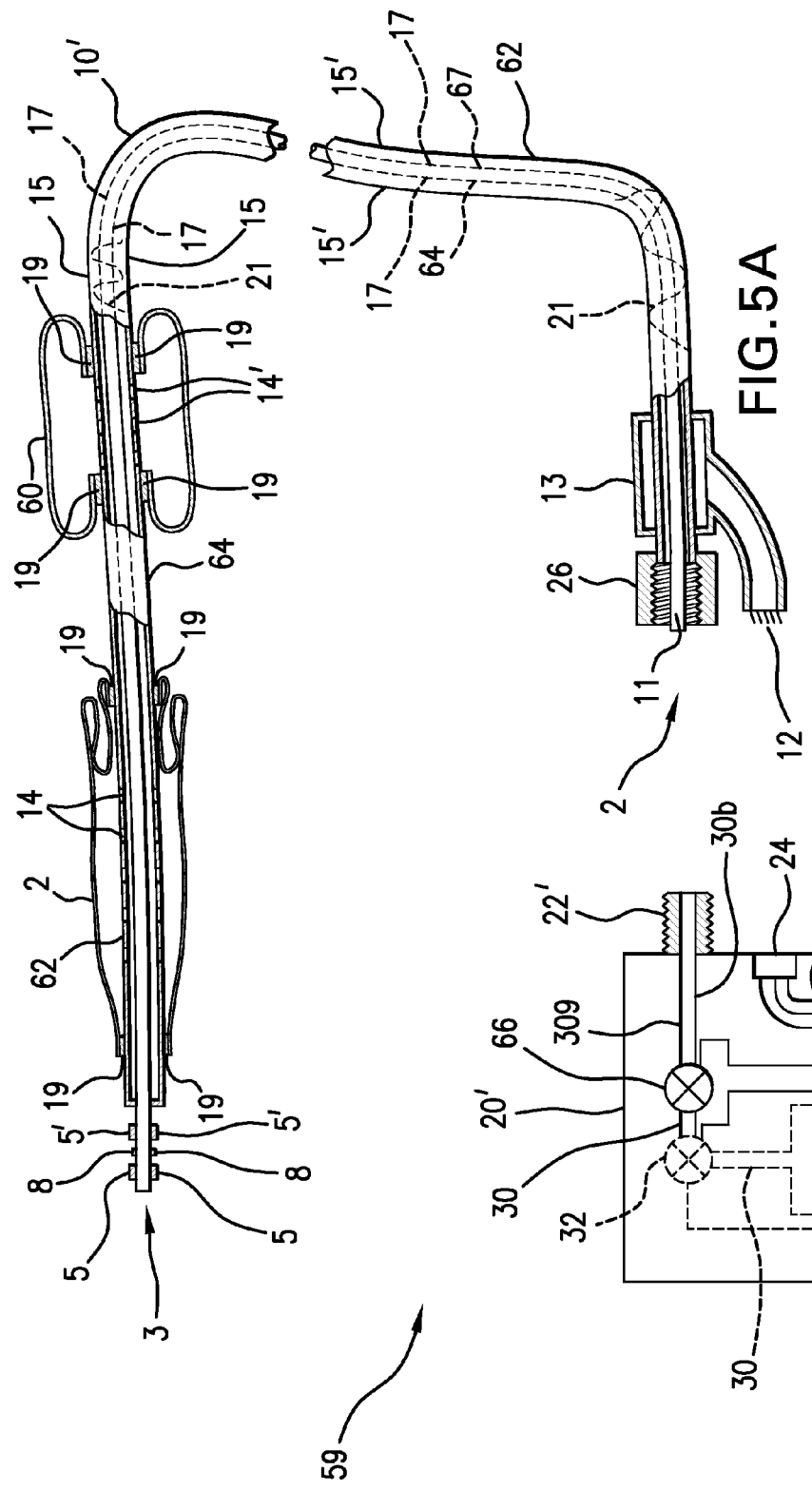

DOUBLE BALLOON PUMP CARDIAC ASSIST DEVICE AND RELATED METHOD OF USE

This application is a continuation-in-part of U.S. application Ser. No. 11/788,887 filed Apr. 23, 2007 now U.S. Pat. No. 8,221,303 claiming benefit of U.S. provisional application No. 60/794,091 filed Apr. 24, 2006, which are incorporated herein in its entirety by reference.

FIELD OF THE INVENTION

This invention relates to cardiac assist devices and their related method of use. More particularly, a left ventricular balloon and an intra aortic balloon are used simultaneously and inflated and deflated to mechanically assist a failing heart in either acute or permanent situations.

BACKGROUND OF THE INVENTION

It is known in the art to provide cardiac assistance by introducing a balloon into the thoracic aorta of a patient and causing the balloon to inflate during diastole and deflate during systole. An extracorporeal pumping unit inflates and deflates the balloon in coordination with the electrocardiogram (ECG), with a suitable neutral drive gas, such as helium. Electrocardiograph leads provide timing information, such as the R wave, to identify systole and a pressure sensor at the catheter tip provides arterial pressure waveforms. This information is used to time the inflation and deflation, and to assess the hemodynamic effects of the treatment. Intra-aortic balloons are disclosed, for example, in U.S. Pat. No. 6,468,200 to Fischi, and U.S. Pat. No. 4,692,148 to Kantrowitz, et al.

U.S. Pat. Nos. 4,685,446, 4,771,765 and 4,902,273 to Choy et al. describe various heart assist devices. The Choy patents define a balloon which is inflated at the very early stages of the systolic phase and as a consequence the energy exerted is destructive. The heart muscle and the balloon are working in opposite directions, thus leading to damage of the *muscle and reduced cardiac output due to physical obstruction of the left ventricular outflow tract The shapes of the Choy devices can unexpectedly cause unpredicted damage.

Advantage of the present invention device and related method and system is in the provision of a specifically shaped device that is inflated within the ventricle at the end of the slow ejection phase of the beating heart. This phase corresponds to the ascending part of the ECG-T wave of the heart. Therefore the energy exerted by the balloon is not contradicting the natural muscle power of the beating heart but only displacing the residual volume of blood and fluid (which are the direct consequence of heart failure) at the end of the muscle contraction. Further more, the balloon is not obstructing the normal ejecting phase of the heart as it does when inflated in early systolic phase as described in the Choy et al. devices.

The double balloon device of the invention provides the simultaneous use of an intra-aortic balloon which reduces the load on the left ventricle and raises aortic pressure to increase the blood flow to the coronary and carotid arteries. This can reduce the pulmonary capillary wedge pressure by approximately 20%, and can decrease aortic systolic pressure by 10% to 20%. Mean arterial pressure can increase by 30 to 40% secondary to enhanced diastolic blood pressure, and both cardiac output and stroke volume may experience a moderate increase.

An intra-aortic balloon may be indicated for several conditions, such as cardiogenic shock; as an adjunct to thrombolysis or percutaneous transluminal coronary angioplasty (PTCA) in acute myocardial infarction (AMI) to maintain vessel patency; prior to coronary artery bypass graft surgery in high risk patients; severe mitral regurgitation (mitral valve too loose); decompensated mitral stenosis (mitral valve too tight); as a bridge to transplant (if an organ is readily available); refractory congestive heart failure; mechanical complication of AMI, i.e., mitral regurgitation due to papillary involvement or ventricular septal defect; or unstable angina refractory to medical therapy.

SUMMARY OF THE INVENTION

The present invention provides a left ventricular balloon and an intra aortic balloon which are used simultaneously and inflated and deflated to mechanically assist a failing heart. The intra-ventricular component of the invention includes a slender flexible catheter having an inflatable balloon mounted near the distal end. The proximal end of the catheter is connected to a control unit containing a bladder in fluid communication with the balloon via a lumen in the catheter. A bidirectional pump in the control unit conducts a fluid, such as helium gas, between the bladder and the balloon in order to effect intermittent inflation of the balloon.

The intra-aortic component of the invention is mounted on a catheter proximally to the intra-ventricular balloon. In acute situations the double balloon is preferably introduced to the femoral artery into the left ventricle and aorta. In a permanent embodiment the catheter is introduced directly into the aorta through a left mini non-invasive thoraectomy. The intra-ventricular balloon is directed into the left ventricle and the intra-aortic balloon is positioned into the aorta just below the subclavian artery.

The control unit further includes a processor that receives electrical signals from electrodes and a pressure sensor disposed at the distal end the catheter. The processor is configured to analyze the signals and to operate the pump so as to coordinate inflation and deflation of the balloon with the cardiac cycle, and to achieve predetermined intra-ventricular systolic and diastolic blood pressure.

When the balloon is properly positioned in the left ventricle, the electrodes contact the wall of the heart and generate signals indicative of the electrical activity that are input to the processor. The-processor is configured to analyze the signals and to identify the ascending part of the T wave of the ECG. When the ascending part of the T wave has been identified by the processor, the processor activates the pump to transfer fluid from the bladder to the balloon so as to inflate the balloon at the beginning of the T wave corresponding to the end of the slow ejection phase of the left ventricle pressure curve. The residual volume of blood left in the left ventricle is displaced through the aortic valve to achieve complete emptying of the left ventricle, increasing the stroke volume and generating additional systolic wave referred to herein as "systolic augmentation". The-processor is also configured to analyze the signals and to identify the descending part of the T wave. When the descending part of the T wave has been identified by the processor, the processor activates the pump to transfer fluid from the balloon to the bladder so as to deflate the balloon just prior to the dicrotic notch.

The system and method of the invention may be indicated for any condition indicated for treatment with an intra-aortic balloon. The system and method of the invention may also be indicated, for example, in individuals suffering from end stage left ventricular failure.

Thus, in one of its aspects, the present invention provides a system for cardiac assist of a heart comprising:

(a) a catheter having a proximal end and a distal end, the catheter having at least one lumen; and (b) an inflatable intra-ventricular balloon mounted on the catheter near the distal end of the catheter, the balloon having a lumen in fluid communication with the lumen of the catheter and being configured for inflation in a ventricle.

The invention also provides an intra-ventricular balloon for use in the system of the invention.

The invention further provides a method for cardiac assist of a heart comprising:

(a) Providing a catheter having a proximal end and a distal end, the catheter having at least one lumen; and an inflatable balloon mounted on the catheter near the distal end of the catheter, the balloon having a lumen in fluid communication with the lumen of the catheter and being configured for inflation in a ventricle;

(b) Delivering the balloon to a ventricle of the heart; and (c) During one or more cardiac cycles, transiently inflating the balloon to achieve a predetermined intra-ventricular systolic pressure.

Other objects, features and advantages of the present invention will be apparent when the detailed description of the preferred embodiments of the invention are considered with reference to the drawings, which should be construed in an illustrative and not limiting sense.

BRIEF DESCRIPTION OF THE DRAWINGS

FIG. 3A illustrates the device in an un-inflated state and FIG. 3B illustrates the device in an inflated state;

FIG. 5A shows an intra-ventricular device in an un-inflated state in accordance with another embodiment of the invention and FIG. 5B is a schematic illustration of the related intra-ventricular cardiac assist system;

FIG. 6A illustrates the deflated IVB and inflated IAB (diastolic phase); and FIG. 6B illustrates the inflated IVB and deflated IAB. (late systolic phase)

DETAILED DESCRIPTION OF THE INVENTION

In order to understand the invention and to see how it may be carried out in practice, a preferred embodiment will now be described, by way of non-limiting example only, with reference to the drawings.

As used in the specification herein the terms intra-ventricular device and intra-ventricular balloon are used interchangeably and are meant to have the same meaning unless otherwise stated.

Figure 1:
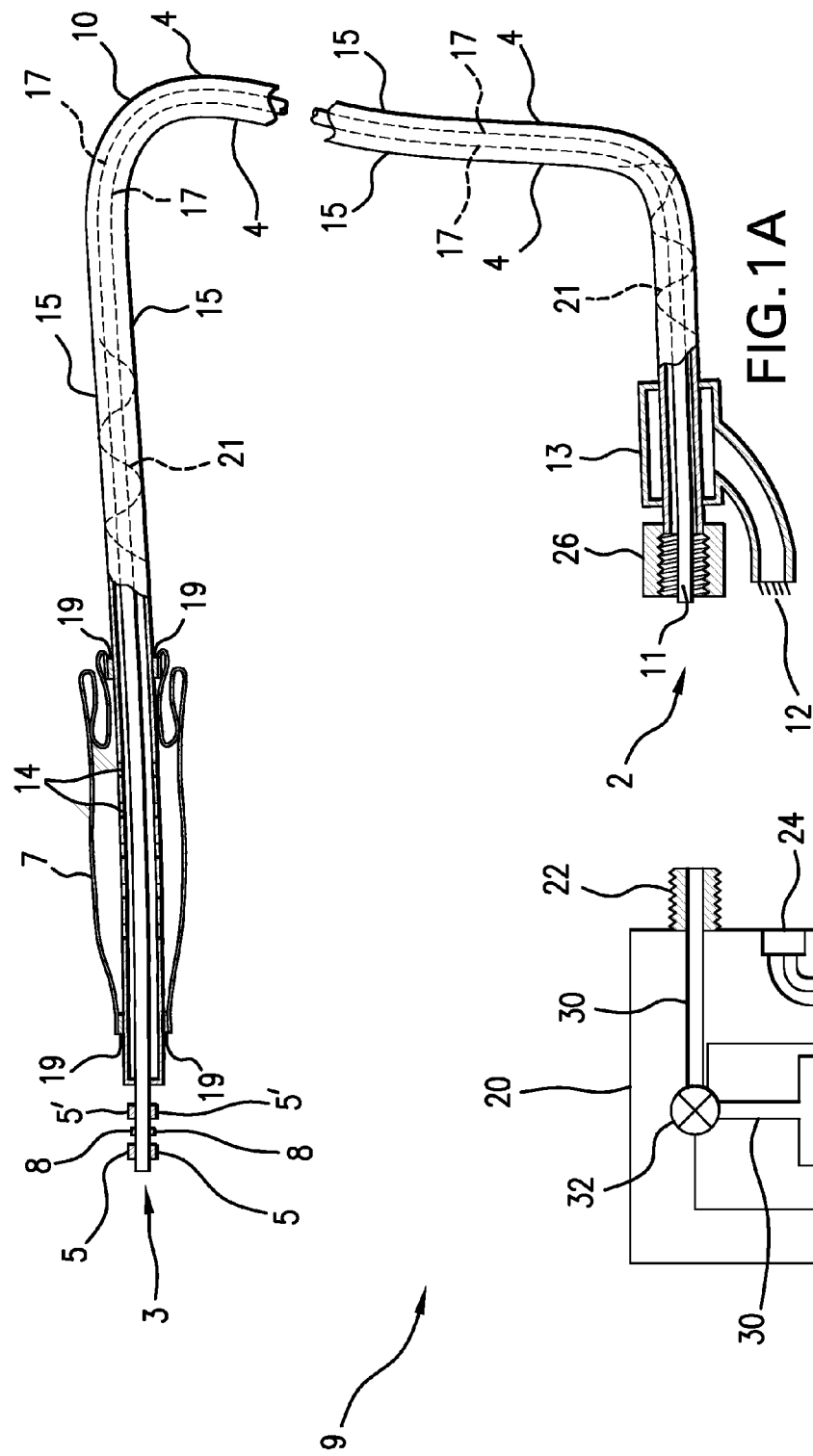
FIG. 1A shows an intra-ventricular device used in the invention in an un-inflated state and FIG. 1B is a schematic illustration of the related intra-ventricular cardiac assist system.

FIG. 1A shows an intra-ventricular balloon and FIG. 1B the related system, generally indicated by 9, in accordance with one embodiment of the invention. The system 9 includes a slender flexible catheter 10 with a proximal end 2 and a distal end 3. An inflatable balloon 7, to be described in detail below, is mounted on the catheter 10 near the distal end 3. The balloon 7 is shown in FIG. 1A in its deflated state and compactly folded onto the outer surface of the catheter 10. The catheter has an outer tubular member 15 and an inner tubular member 17 coaxial with the outer tubular member 15. The balloon 7 is mounted onto the outer tubular member 15 in air tight seals 19 that may be formed, for example, using an adhesive. The outer tubular member 15 has an annular lumen 4 and the wall of the outer tubular member is perforated with a plurality of apertures 14 in the segment of the outer tubular member 15 upon which the balloon 7 is mounted, so that the lumen of the balloon 7 and the lumen 4 are in fluid communication.

The inner tubular member 17 has a distal end that extends beyond the distal end of outer tubular member 15. A pair of spaced apart electrodes 5, 5' is disposed at the distal end 3 of the catheter 10 in the portion of the inner tubular member 17 extending beyond the distal end of the outer tubular member 15. A pressure transducer 8 is disposed between the electrodes 5, 5'. At the proximal end 2 of the catheter is a coupling 13 having a fluid supply port 11 and electric terminals 12. Individual lead wires 21 are helically wound along the luminal surface of the catheter 10 and connect each of the electrodes 5, 5' and the pressure transducer 8 to terminals in the plug 12.

The system 9 also includes a control unit 20. The control unit 20 includes a fluid port 22 and an electrical socket 24. The fluid port 22 of the control unit is adapted to mate with the fluid port 11 of the catheter 10. A locking nut 26 associated with the port 11 screws onto an outer threaded surface of the port 22 to create a fluid tight seal between the ports 11 and 22. The electrical socket 24 is adapted to mate with the plug 12 of the catheter 10.

The fluid port 22 is in fluid communicating with a bladder 28 inside the control unit 20 via a tube 30. The bladder 28 functions as a fluid reservoir. The bladder 28, the tube 30, the lumen 4 and the balloon 7 thus form a closed fluid conduction system when the ports 11 and 22 are mated. The fluid conduction system is provided with a volume of a fluid, that may be, for example, helium gas. A bidirectional pump 32 conducts fluid in the fluid conduction system between the bladder 28 and the balloon 7. When fluid is conducted by the pump 32 from the bladder 28 to the balloon 7, the balloon 7 inflates while the bladder 28 deflates. When fluid is conducted by the pump 32 from the balloon 7 to the bladder 28, the bladder 28 inflates while the balloon 7 deflates.

The control unit 20 further includes a processor 34. The processor 34 receives electrical signals from the electrodes 5 and 5' and the pressure sensor 8 via the leads 21 in the catheter 10 and leads 36 in the control unit 20 when the plug 12 is mated with the socket 24. The processor 34 is configured to analyze the signals and to operate the pump 32 via a control line 40, so as to coordinate inflation and deflation of the balloon 7 with the cardiac cycle, as explained below. A power supply 42, such as a battery, provides electrical power to the processor 34 and the pump 32.

Figure 2:
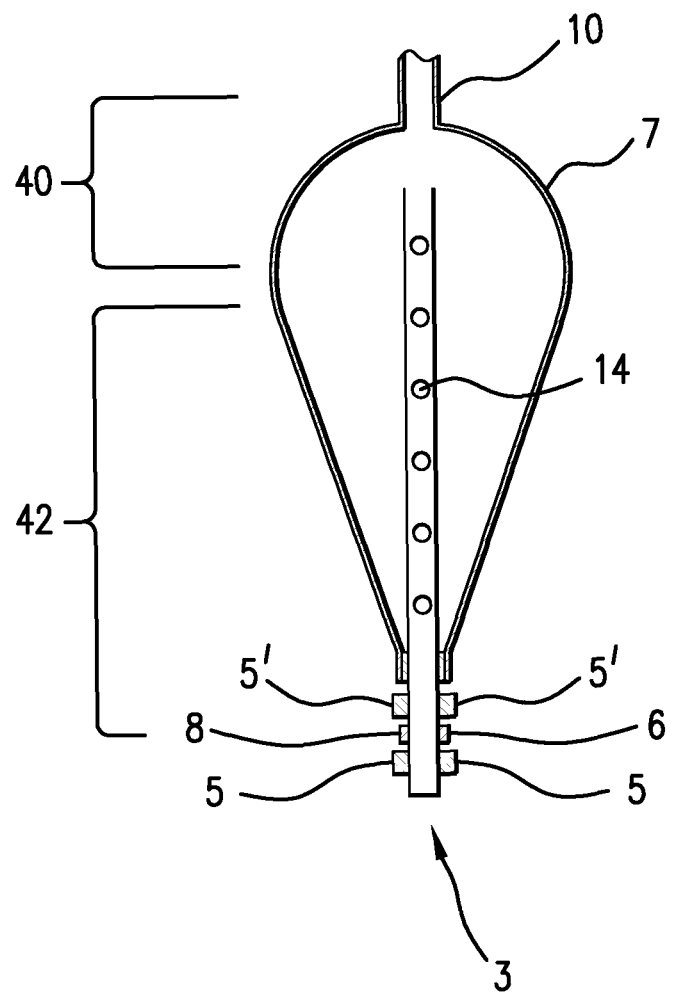
FIG. 2 shows the intra-ventricular device of the system in FIG. 1 in an inflated state.

The balloon 7 may be made from any fluid impervious material, and may have any shape, as required in any particular application. The shape of the balloon 7 is preferably selected so as to avoid interference with the sub-apparatus of the mitral valve or the semi-lunar valve. In one preferred embodiment shown in FIG. 2, the balloon 7 when inflated has a shape comprising a proximal hemispherical portion 40 and a distal conical portion 42. This shape approximates the lumen of the left ventricle. This predetermined ice cream cone shape allows the following advantages: a) minimal interference with the submitral apparatus as well as the semilunar valve. b) minimal pressure on the left ventricular wall. c) maximal ejection force directed toward left ventricular outflow tract, to facilitate perfect emptying of the left ventricle.

In order to deliver the balloon 7 to the left ventricle, the distal end of a guide wire is inserted into the femoral artery of an individual and navigated through the arterial system to the aorta and then into the left ventricle via the aortic semilunar valve. The proximal end of the guide wire is then inserted into the distal end of the lumen of the inner tubular member 17 and slid to the proximal end of the catheter 10. The catheter 10, with the balloon 7 deflated and compactly folded around it, is then guided along the guide wire until the balloon 7 is positioned in the left ventricle.

Figure 3A:
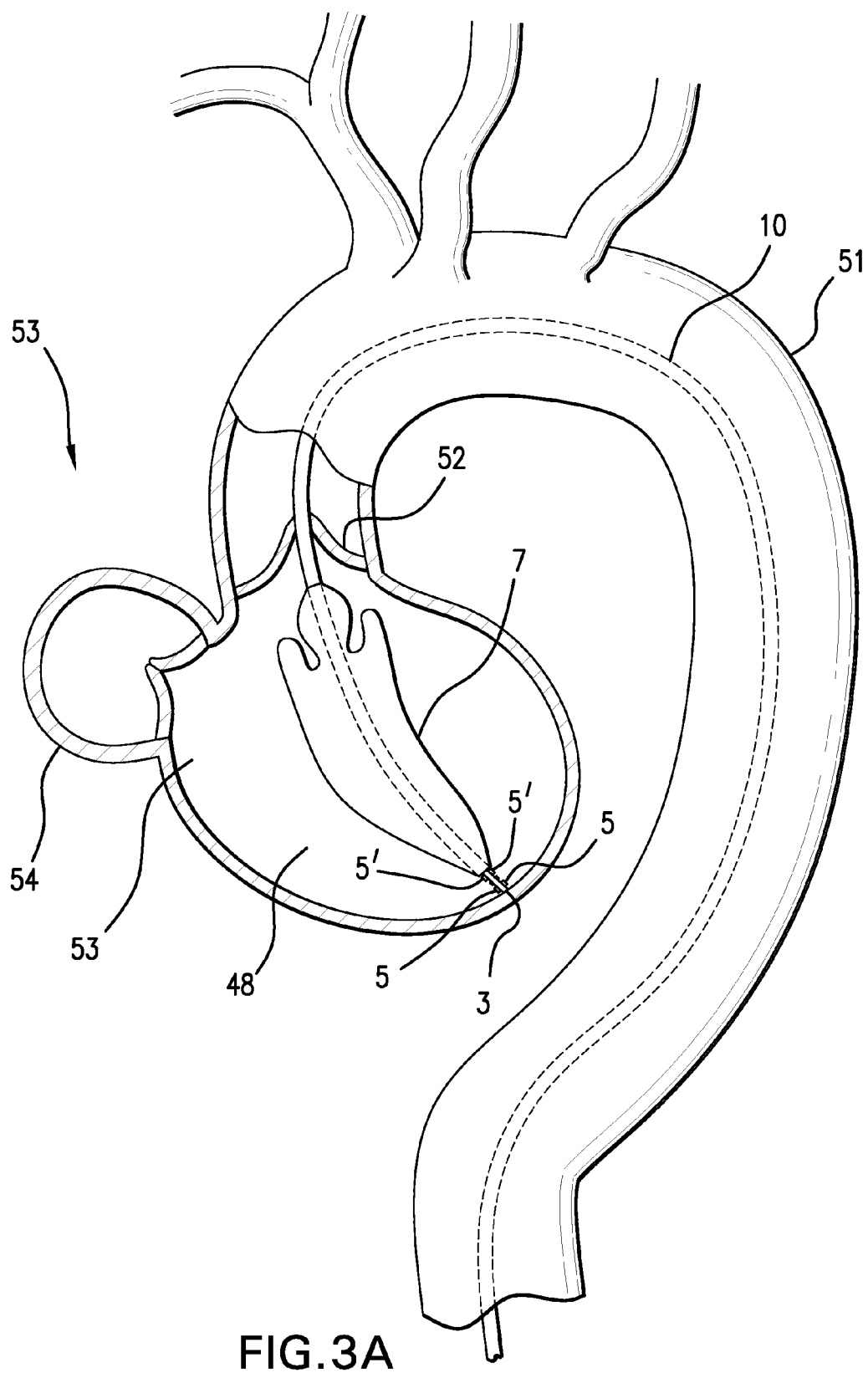
FIG. 3A and FIG. 3B shows positioning of the intra-ventricular device of FIG. 1 in a left ventricle, more particularly
Figure 3B:
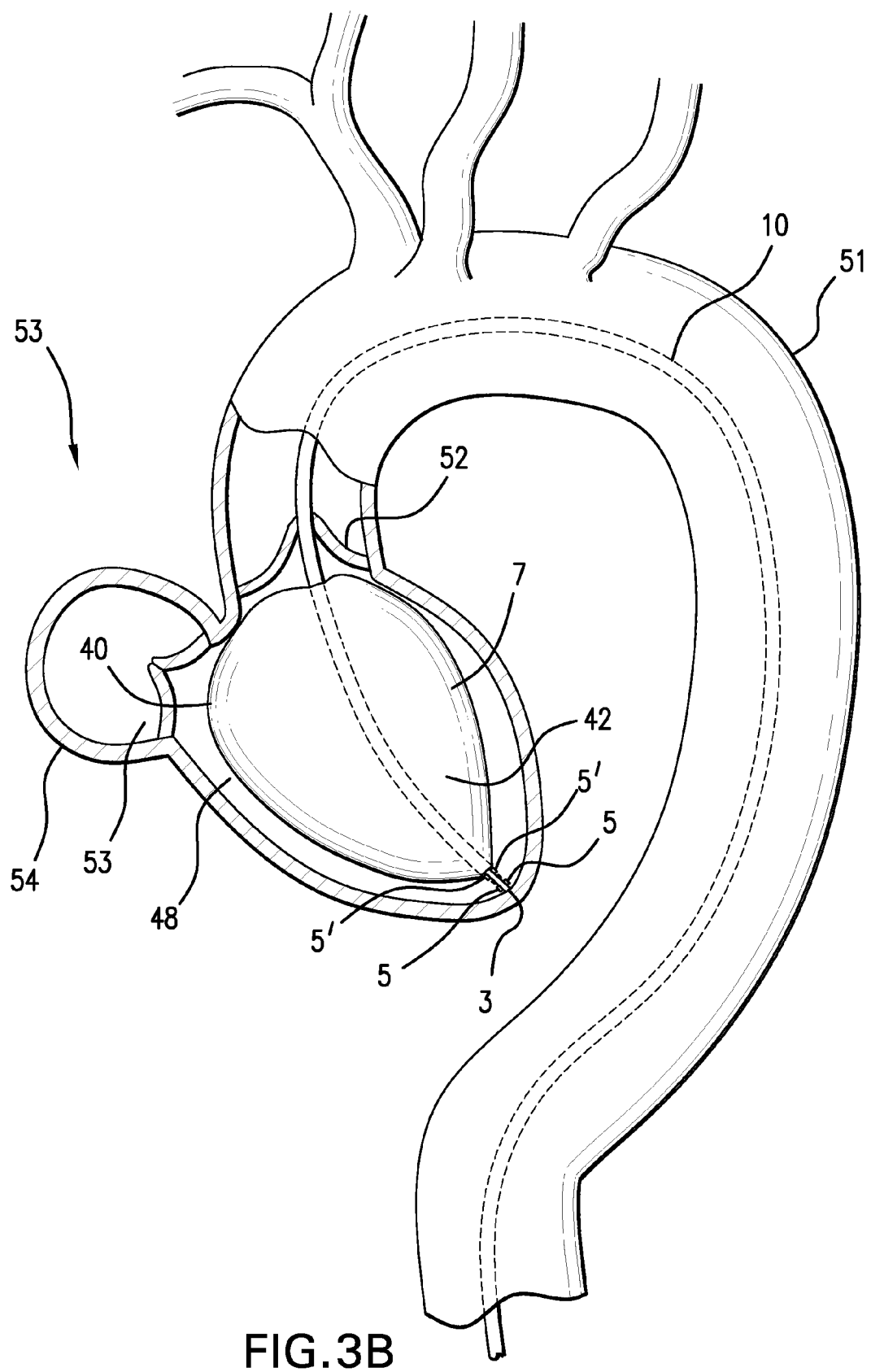

FIGS. 3A and 3B shows proper positioning of the distal end 3 of the catheter 10 in the left ventricle 48 of a heart 53, only a portion of which is shown in FIGS. 3A and 3B. The catheter 10 passes through the aorta 51, through the semilunar aortic valve 52 and into the left ventricle 48. The left ventricle is separated from the left atrium 54 by the mitral valve 53. The balloon 7 is shown in FIG. 3A positioned in the left ventricle 48 in its deflated state. As the balloon 7 is brought into the position in the left ventricle the electrodes 5 and 5' contact the wall of the left ventricle. Upon contacting the wall of the left ventricle, signals indicative of the electrical activity are generated that are input to the processor 34. This provides an indication that the distal end 3 of the catheter 10 is properly positioned in the left ventricle. Thus, the catheter may be properly positioned without recourse to x-ray images of the catheter. After proper positioning of the balloon in the left ventricle, as shown in FIG. 3A, the guide wire is withdrawn from the individual's body through the lumen of the tubular member 17.

The processor 34 is configured to analyze the ECG signals generated across the electrodes 5 and 5' and to identify a first predetermined feature of each heartbeat form. When the first predetermined feature of the ECG signal has been identified by the processor 34, the processor activates the pump 32 to transfer fluid from the bladder 28 to the balloon 7 so as to inflate the balloon. In a preferred embodiment of the invention, the first predetermined feature is the beginning of the T wave. When the balloon 7 has the inflated shape described above in reference to FIG. 2, the inflated balloon is positioned in the left ventricle 48 with the hemispherical portion 40 just below the aortic semi-lunar valve 52 in FIG. 3B. The tip of the conical portion 42 is situated at the apex of the left ventricle 48. The middle portion of the balloon 7 is situated in the mid portion of the ventricle in such a way as to avoid interference with the sub-apparatus of the mitral valve. Any inflation prior to the end of the slow ejection phase would result in decreased cardiac output, and rather than increased output. The processor 34 is also configured to analyze the ECG signals across the electrodes 5 and 5' and to identify a second predetermined feature in each heartbeat form. When the second predetermined feature has been identified by the processor, the processor activates the pump 32 to transfer fluid from the balloon 7 to the bladder 28 so as to deflate the balloon. In a preferred embodiment of the invention, the second predetermined feature is descending part of the T wave just prior to the dicrotic notch.

In a preferred embodiment the proximal part of the electrodes can be connected to a pacemaker box. When a patient has a heart block or goes into cardiac arrest the pacemaker can be activated and instant pacing achieved. This instantaneous activation is expected to enhance survival of these conditions and circumstances. The processor can then identify the T-Wave signals and LV assistance through the IVB and IVA/IAB is accomplished.

Figure 4:
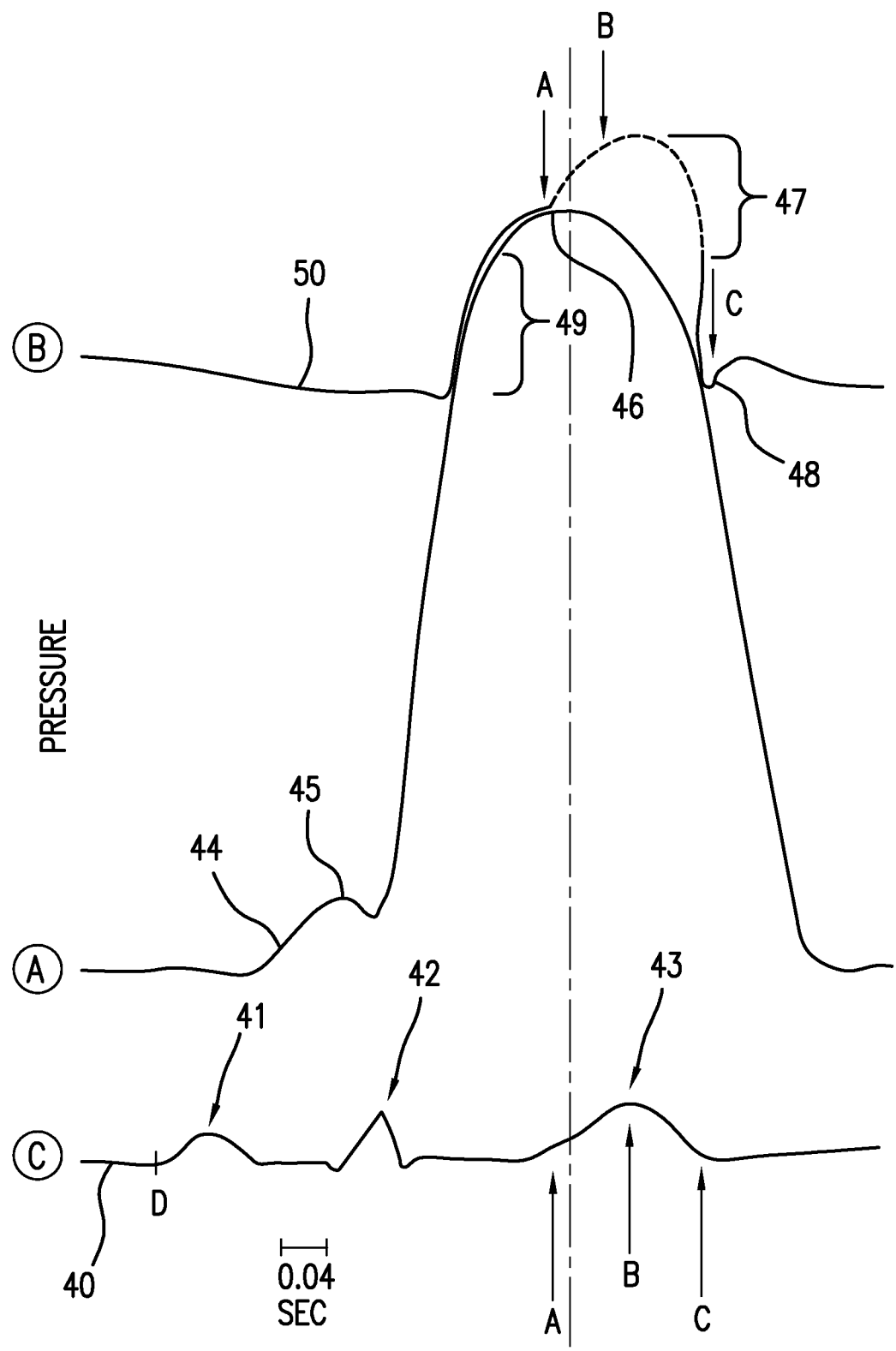
FIG. 4 shows the inflation-deflation cycle of the intra-ventricular device and related system according to the invention in relation to the ECG signal (C) and in relation to left ventricular (A) and aortic (B) pressure.

FIG. 4 shows the pumping cycle of the balloon 7, in relation to the ECG signal, in accordance with a preferred embodiment of the invention. As illustrated in the figure, the curve labeled A shows the left ventricular pressure, the curve labeled B shows the aortic pressure and the curve labeled C shows the ECG signal. A typical heartbeat form 40 of an ECG signal has a P wave 41, a QRS complex 42, and a T wave. 43. The left ventricular pressure curve 44 has a first spike 45, following the P wave 41, that is followed by a second larger spike 46 extending from the QRS complex 42 until after the T wave 43. The aortic pressure curve 50 rises during the rapid ejection phase 49 of the left ventricular pressure curve 44. As explained above, in a preferred embodiment of the invention, the balloon 7 is inflated at the beginning of the T-wave which corresponds to the end of the slow ejection phase of the left ventricular pressure curve (the point A in FIG. 4) As a consequence, the residual volume of blood in the left ventricle is displaced through the aortic valve to the aorta generating a second peak in the aortic pressure, referred to herein as "systolic augmentation". 47. Also in accordance with a preferred embodiment of the invention, deflation of the balloon 7 commences at the peak of the T-wave which corresponds to the peak of the systolic augmentation (the point B). This allows the pressure to drop in the left ventricle to facilitate closure of the aortic valve is at the dicrotic notch 48 (the point C). Deflation of the balloon is completed at the end of the T-wave which corresponds to the dicrotic notch (aortic valve closure) 48.

A healthy left ventricle typically ejects in each cycle 60-70% of the blood received from the left atrium through the mitral valve. A failing left ventricle may eject as little as 20-30% of the received blood in each cycle, a condition known as "left ventricular failure". By inflating the balloon 7 at the end of the slow ejection phase, (the point A) the residual volume in the left ventricle is displaced through the aortic valve to the aorta generating the systolic augmentation. This leads to an increase in cardiac output that may be as high as 100%. The volume of the inflated balloon is preferably to match perfectly the left ventricle size and shape to optimize the augmentation and prevent floating of the balloon.

The volume of the balloon 7 when inflated is determined in accordance with the volume of the left ventricle, and is typically in the range of 40-60 ml. The processor 34 receives signals indicative of the intra-ventricular pressure from the pressure transducer 8. The signals received by the processor from the pressure transducer 8 allow the processor to monitor the blood pressure. The processor is configured to adjust the activity of the pump 32 to regulate the inflation volume of the balloon, the inflation rate, and the deflation rate in order to achieve predetermined intra-ventricular systolic and diastolic pressures. The predetermined pressures may be input to the processor using an input device such as a keyboard 43. The fluid pressure inside the inflated balloon is typically around 9-10 psi.

In a preferred embodiment, the processor 34 is configured to identify the occurrence of cardiac arrest. The system 9 is adapted to apply voltages across the electrodes 5 and 5' in order to pace the heart when cardiac arrest occurs. The pump 32 can be implanted under the skin and provided with a wireless, rechargeable mechanism. In a preferred embodiment, the pump is portable and rechargeable. As mentioned it can be implanted under the skin for chronic use in end stage left ventricular failure.

FIG. 5A shows an intra-ventricular balloon and FIG. 5B illustrates the related system, generally indicated by 59, in accordance with another embodiment of the invention. The system 59 has several components in common with the system 9, and similar components in the two systems are indicated by the same reference numeral without further comment. The system 59 includes a slender flexible catheter 10' with a proximal end 2' and a distal end 3'. As with the system 9, the system 59 includes the inflatable balloon 7 mounted on the catheter 10' near the distal end 3'. In addition, the system 59 includes a second inflatable balloon 60 mounted on the catheter 10' proximally to the balloon 7. The balloons 7 and 60 are shown in FIG. 5 in their deflated state and compactly folded onto the outer surface of the catheter 10'. The balloons 7 and 60 are spaced apart along the catheter 10'; so that the distal balloon 7 can be positioned in the left ventricle, as explained above in reference to the system 9, while the balloon 60 is positioned in the descending aorta. The balloons 7 and 60 are mounted onto the outer tubular member 15' in air tight seals 19 that may be formed, for example, using an adhesive. The catheter 10' has an outer tubular member 15' containing three lumens. A lumen 62 is perforated with a plurality of apertures 14 in the segment of the lumen 62 upon which the balloon 7 is mounted, so that the lumen of the balloon 7 and the lumen 62 are in fluid communication. A lumen 64 is perforated with a plurality of apertures 14' in the segment of the lumen 64 upon which the balloon 60 is mounted, so that the lumen of the balloon 60 and the lumen 64 are in fluid communication The system 59 also includes a control unit 20'. The control unit 20' includes a fluid port 22' and the electrical socket 24. The fluid port 22' of the control unit is adapted to mate with a fluid port 11' of the catheter 10'. A locking nut 26 associated with the port 11' screws onto an outer threaded surface of the port 22 to create a fluid tight seal between the ports 11' and 22'. The electrical socket 24 is adapted to mate with the plug 12 of the catheter 10.

The lumens 62 and 64 of the catheter 10 are in fluid communicating with the bladder 28 inside the control unit 20' via a first tube 30a and a second tube 30b, respectively. As in the system 9, the bladder 28 of the system 59 functions as a fluid reservoir. The bladder 28, the tube 30a, the lumen 62 and the balloon 7 form a first closed fluid conduction system when the ports 11' and 22' are mated. The bladder 28, the tube 30b, the lumen 64 and the balloon 60 form a second closed fluid conduction system when the ports 11' and 22' are mated. The fluid conduction system is provided with a volume of a fluid, that may be, for example, helium gas. The system 59 includes a solenoid valve 66 situated where the tube 30' bifurcates into the tubes 30a and 30b. Depending on the position of the solenoid valve 66, the bidirectional pump 32 conducts fluid in the fluid conduction system between the bladder 28 and the balloon 7 via the tube 30a or between the bladder 28 and the balloon 60 via the tube 30b. When fluid is conducted by the pump 32 from the bladder 28 to the balloon 7 or the balloon 60, the balloon 7 or 60 inflates while the bladder 28 deflates. When fluid is conducted by the pump 32 from the balloon 7 or the balloon 60 to the bladder 28, the bladder 28 inflates while the balloon 7 or 60 deflates.

The control unit 20 further includes a processor 34'. The processor 34' receives electrical signals from the electrodes 5 and 5' and the pressure sensor 8 via the leads 21 in the catheter 10' and leads 36 in the control unit 20 when the plug 12 is mated with the socket 24. The processor 34 is configured to analyze the signals and to operate the pump 32 via a control line 40a, and the valve 66 via a control line 40b so as to coordinate inflation and deflation of the balloons 7 and 60 with the cardiac cycle, as explained below. A power supply 42, such as a battery, provides electrical power to the processor 34 and the pump 32, and the valve 66.

The balloons 7 and 60 may be made from any fluid impervious material, and may have any shape, as required in any particular application. In one preferred embodiment the balloon 7 have the shape shown in FIG. 2. The balloon 60 may have any shape known in the art for intra-aortic balloons. The intra-aortic balloons are of a pre-determined shape and are inflated during the diasystolic phase.

Although it has been stated previously the timing of the inflation of the intra-ventricular device is important to the success of the invention method, the particular shape of the balloon is critical also. In preferred embodiments the pre-determined shape of the balloon is similar to an ice-cream cone shaped, having a hemispherical proximal end and a tapered distal end. The tapered distal end is preferably semi-rigid to enable proper placement within the ventricle. Upon inflation the top portion expands to the size of the entire ventricle and pushes the residual blood from the space.

The particular shape and design of the invention device allows minimal lateral wall pressure, with most of the energy directed towards the ventricle outflow track. This optimizes the direction of blood-flow.

In contrast to known heart assist devices as described in the Choy et al. patents the invention balloon does not use mercury to achieve neutral buoyancy at inflation. In the invention method, the perfect matching between the left ventricle and the intra-ventricular balloon (IVB) prevents floating of the balloon.

Different sizes of the invention balloons are provided to match different sizes of ventricles. For example, chronic failure left ventricles can be dilated and therefore would accommodate bigger balloons in order to get optimal displacement. Smaller ventricles would have proportionally smaller balloons to avoid interference with mitral, aortic and left ventricular wall structures.

In order to deliver the balloons 7 to the left ventricle and the balloon 60 to the aorta, the distal end of a guide wire is inserted into the femoral artery of an individual and navigated through the arterial system to the aorta and then into the left ventricle via the aortic semilunar valve. The proximal end of the guide wire is then inserted into the distal end of a lumen 67 of the inner tubular member 17 and slid to the proximal end of the catheter 10'. The catheter 10', with the balloons 7 and 60 deflated and compactly folded around it, is then guided along the guide wire until the balloon 7 is positioned in the left ventricle and the balloon 60 is positioned in the descending aorta.

Figure 6A:
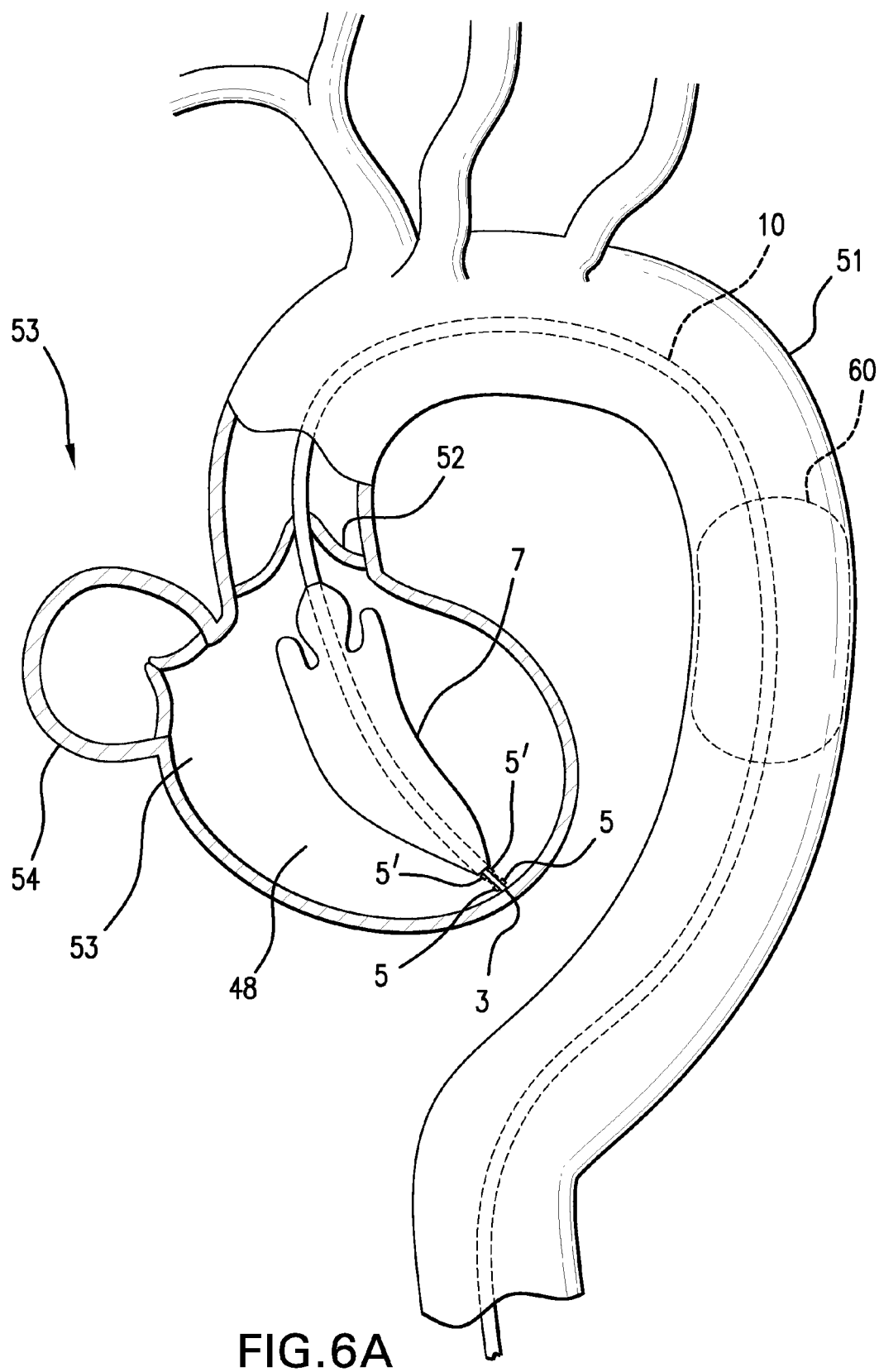
FIG. 6A and FIG. 6B shows the combination of the intra-ventricular balloon ("IVB") with intra aortic balloon ("IAB") in Type A acute situations.
Figure 6B:
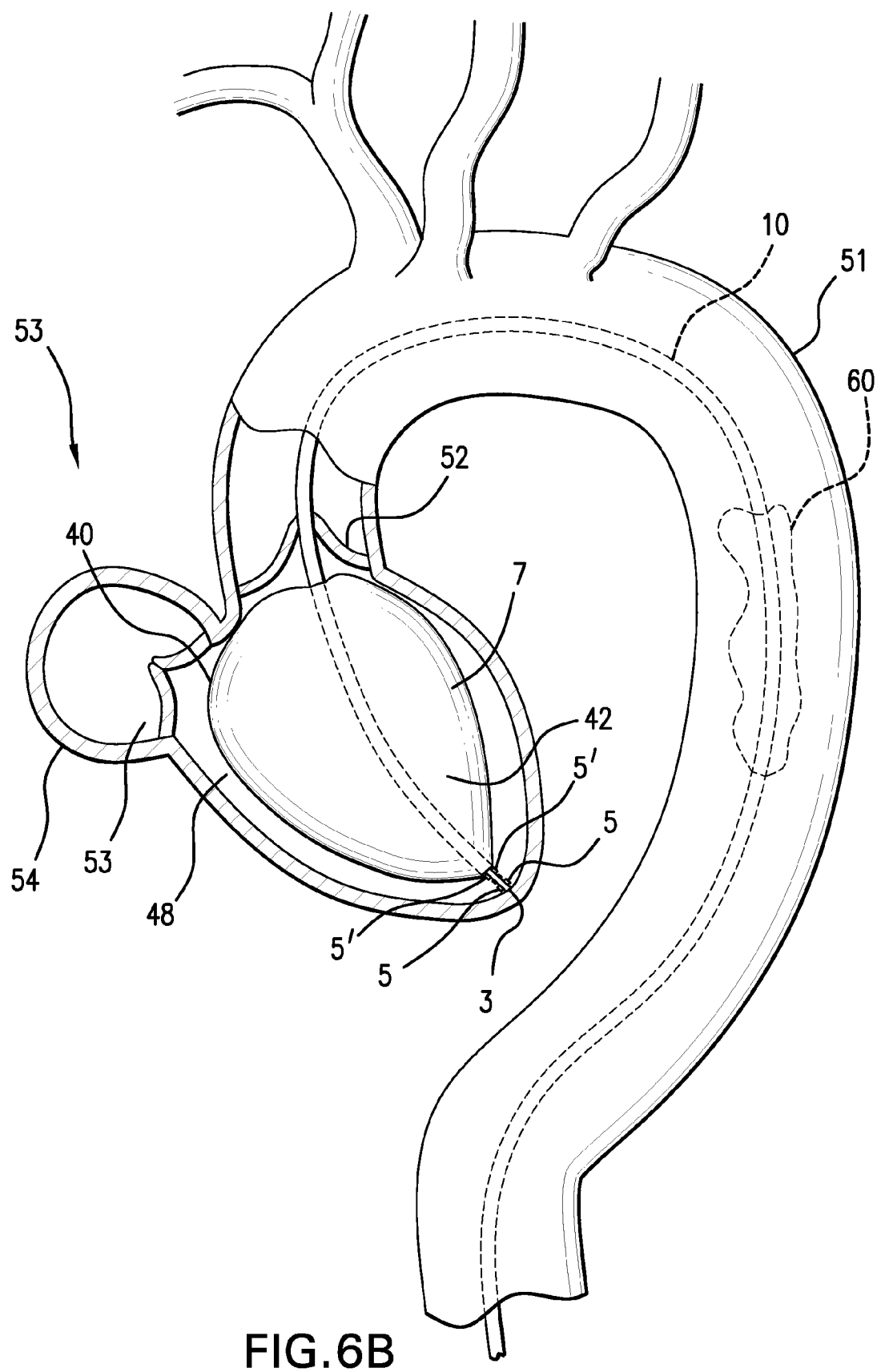

FIGS. 6A and 6B show proper positioning of the distal end 3 of the catheter 10' in the left ventricle 48 of a heart 53, only a portion of which is shown in the figures. The balloons 7 and 60 are shown in FIG. 6A positioned in the left ventricle 48 and the aorta 51, respectively, in their deflated and inflated state. As the balloon 7 is brought into the position in the left ventricle, the electrodes 5 and 5' contact the wall of the left ventricle. Upon contacting the wall of the left ventricle, signals indicative of the electrical activity are generated that are input to the processor 34. This provides an indication that the balloon 7 is properly positioned in the left ventricle and the balloon 60 is properly positioned in the descending aorta. Thus, the catheter 10' may be properly positioned without recourse to x-ray images of the catheter. After proper positioning, as shown in FIG. 6A, the guide wire is withdrawn from the individual's body through the lumen of the tubular member 17.

FIG. 6B illustrates the tight relationship between the ventricle and the device to achieve the advantages of minimal pressure in the ventricular wall and maximum ejection force toward the left ventricular outflow tract as well as the inability of the balloon to float.

Referring again to FIG. 4, the processor 34 is configured to analyze the ECG signals generated across the electrodes 5 and 5' and to identify a first predetermined feature of each heartbeat form, when the intra-ventricular balloon 7 is to be inflated, a second predetermined feature of each heartbeat form, when the balloon 7 is to be deflated, a third predetermined feature of each heartbeat form, when the intra-aortic balloon 60 is to be inflated, a fourth predetermined feature of each heartbeat form, when the balloon 60 is to be deflated. When the first predetermined feature of the ECG signal has been identified by the processor 34, the processor activates the pump 32 and the solenoid valve 66 to transfer fluid from the bladder 28 to the balloon 7 via the tube 30a so as to inflate the balloon 7. When the second predetermined feature has been identified by the processor, the processor activates the pump 32 and the solenoid valve 66 to transfer fluid from the balloon 7 to the bladder 28 via the tube 30a so as to deflate the balloon 7. When the third predetermined feature of the ECG signal has been identified by the processor 34, the processor activates the pump 32 and the solenoid valve 66 to transfer fluid from the bladder 28 to the balloon 60 via the tube 30b so as to inflate the balloon 60. When the fourth predetermined feature has been identified by the processor, the processor activates the pump 32 and the solenoid valve 66 to transfer fluid from the balloon 60 to the bladder 28 via the tube 30b so as to deflate the balloon 7. The balloons 7 and 60 are shown in FIG. 6B positioned in the left ventricle 48 and the aorta 51, respectively, in their diastolic phase i.e. FIG. 6A illustrates the deflated IVB and inflated IAB.

As with the system 9, in a preferred embodiment of the system 59, the balloon 7 is inflated at the end of the slow ejection phase of the left ventricular pressure (the point A in FIG. 4). Deflation of the balloon 7 commences at the peak of the systolic augmentation (the point B) and is complete when the left ventricular pressure is at the dicrotic notch 48 (the point C). As explained above, this timing of the inflation and deflation of the balloon 7 generates the systolic augmentation 47. Also in accordance with a preferred embodiment, the intra-aortic balloon 60 begins to inflate after closure of the aortic valve (the dicrotic notch 48, point C), and deflation occurs prior to the P wave of the subsequent heart beat (the point D in FIG. 4).

Figure 7:
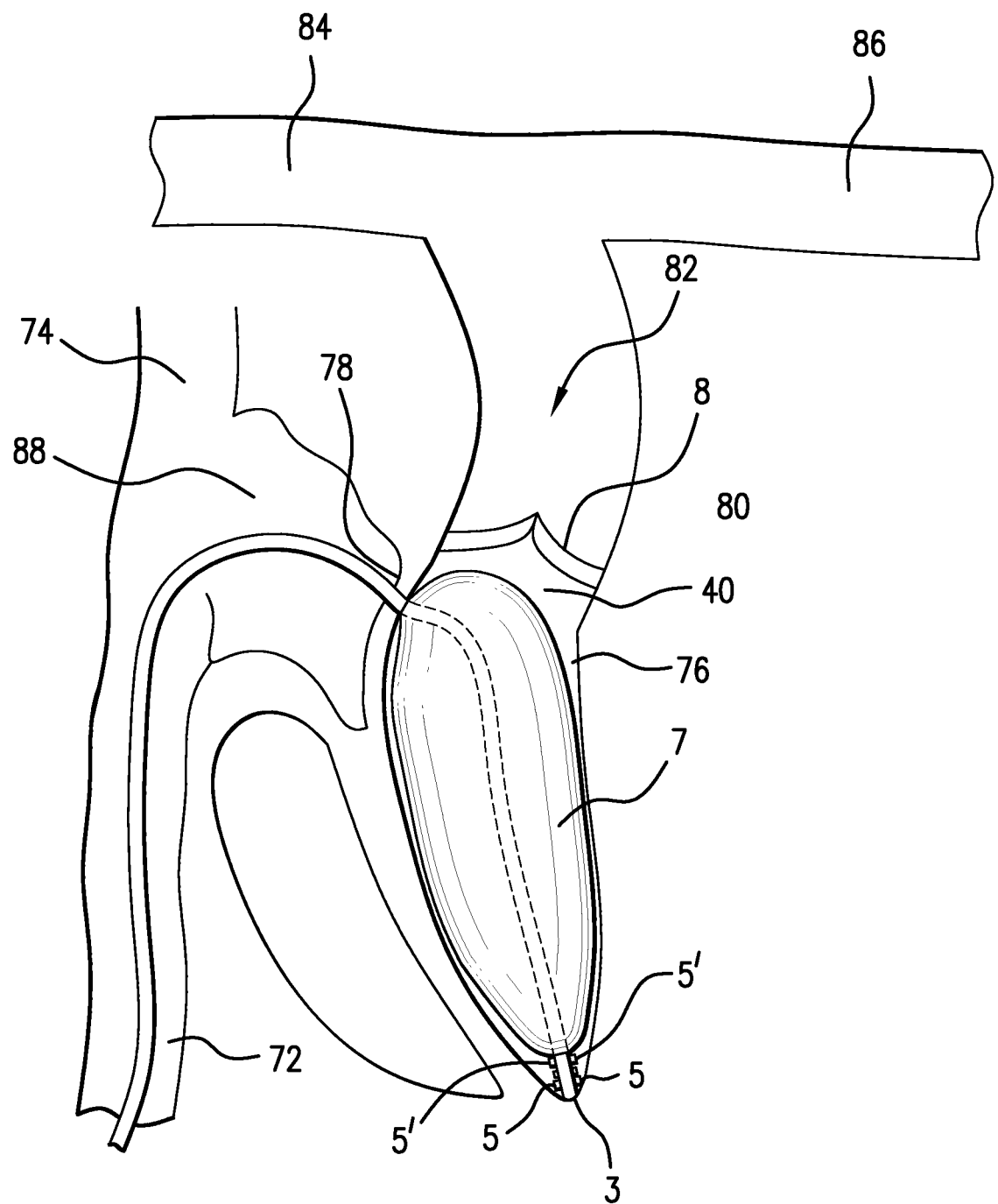
FIG. 7 shows positioning of the intra-ventricular device of FIG. 1 in a right ventricle.

The system of the invention may also be used in a right ventricle. In this case, as shown in FIG. 7, the balloon 7 is inserted into a central vein and delivered to the inferior vena cava 72 or superior vena cava 74, and from there to the right ventricle 76. The balloon 7 is positioned in the right ventricle with the proximal hemispherical portion 40 below the tricuspid valve 78 that separates the right ventricle from the right atrium 88. The balloon is preferably inflated at the end of the slow ejection phase corresponding to the beginning of the ECG T wave, thus displacing residual blood volume through the pulmonary valve 80 and into the main pulmonary artery 82. The main pulmonary artery divides into the right pulmonary artery 84 and the left pulmonary artery 86. The balloon is deflated at the peak of the systolic augmentation.

EXAMPLE 1

A new Left Ventricular Assist Device (L.V.A.D) was designed and tested in an attempt to assist mechanically the failing heart.

Heart failure consists of the inability of the heart to push 70% to 80% of the blood entered the ventricle in each beat leading to accumulation of residual volume within the heart. Inflating a balloon within the ventricle at the end of the systolic phase before closure of the aortic valve occurs will displace the abnormal residual volume restoring normal function of the heart. It was however well understood that inflating the intra ventricular balloon in early stages of the systolic phase (earlier than the end of slow ejection phase) will bring upon catastrophic results due to the fact that the balloon will obstruct the outflow tract thus preventing from the heart the normal ejection.

An intra ventricular balloon ("IVB") preferably designed of a pear shape to avoid any interference with the function of the aortic and mitral valve was tested in the following manner. A machine capable of inflating and deflating the IVB with helium gas through a reservoir connected via a connecting tube was carried out. Synchronization of inflation after the end of slow ejection phase and deflation at the dicrotic notch was established via ECG. Cardiac output was measured through esophageal canola.

Fifty Kg pig was anesthesized and the resting cardiac output was found to be 5 liters/min. The chest was opened and legation of the left anterior descending artery was carried out leading to immediate fall of the cardiac output to 2.7 liters/min due to the massive infarction after legating the left anterior descending artery. The IVB introduced through the femoral artery crossing the aortic valve was positioned in the left ventricle. Timing of inflation and deflation was achieved via the ECG and helium pump was turned on.

Instantly the left ventricle tracing pressure changed. The left ventricle pressure showed a double peak curve as opposed to the normal one peak pressure. The first peak represented the normal ejection phase carried out by the left ventricle contraction whereas the second peak, that was higher than the first peak represented the blood displacement carried out by the balloon and labeled systolic augmentation. The new cardiac output measured minutes after ballooning the failed left ventricle exceeded the control values and reached 5.8 liters/min. This example proves that optimal IVB inflated at the right time can double the cardiac output of the failing heart.

Inflation of intra aortic balloon ("IAB") during diastolic phase was proven to increase cardiac output in 20% due to the after load reduction of the left ventricle by emptying the aorta before next systolic phase occurs, but more importantly due to raised aortic diastolic pressure the I.A.B can increase notably the coronary flow thus improving any failing heart due to ischemia (lack of oxygenated blood). It is therefore understood that the combination of the I.V.B and the I.A.B would bring upon a major added value to the failing heart especially if ischemia is involved. The control system within the box is programmed according to the ECG signals and the L.V pressure curve to inflate the I.V.B at the end of the slow ejection phase and to deflate it at the very end of the systolic phase at the dicrotic notch.

The I.A.B however is being inflated from the very beginning of the diastolic phase to be deflated at the end of the diastolic phase. The left ventricle pressure curve is read by a pressure gauge at the tip of the I.V.B and the ECG is read by a pair of electrodes situated as well at the tip of I.V.B.

DOUBLE BALLOON PUMP DEVICES AND MODE OF INSERTIONS

Two types of devices are disclosed Type A (acute) and Type P (permanent)

Type A is illustrated in FIGS. 6A and 6B and detailed explanations are discussed earlier. This double balloon pump catheter is introduced through the femoral artery into the left ventricle. The other side is being connected to the console situated next to the patient's bed. This type of the device is used when acute left ventricular failure occurs such as acute myocardial infarction or during post operative period when urgent assistance is required and is typically temporary.

Figure 8:
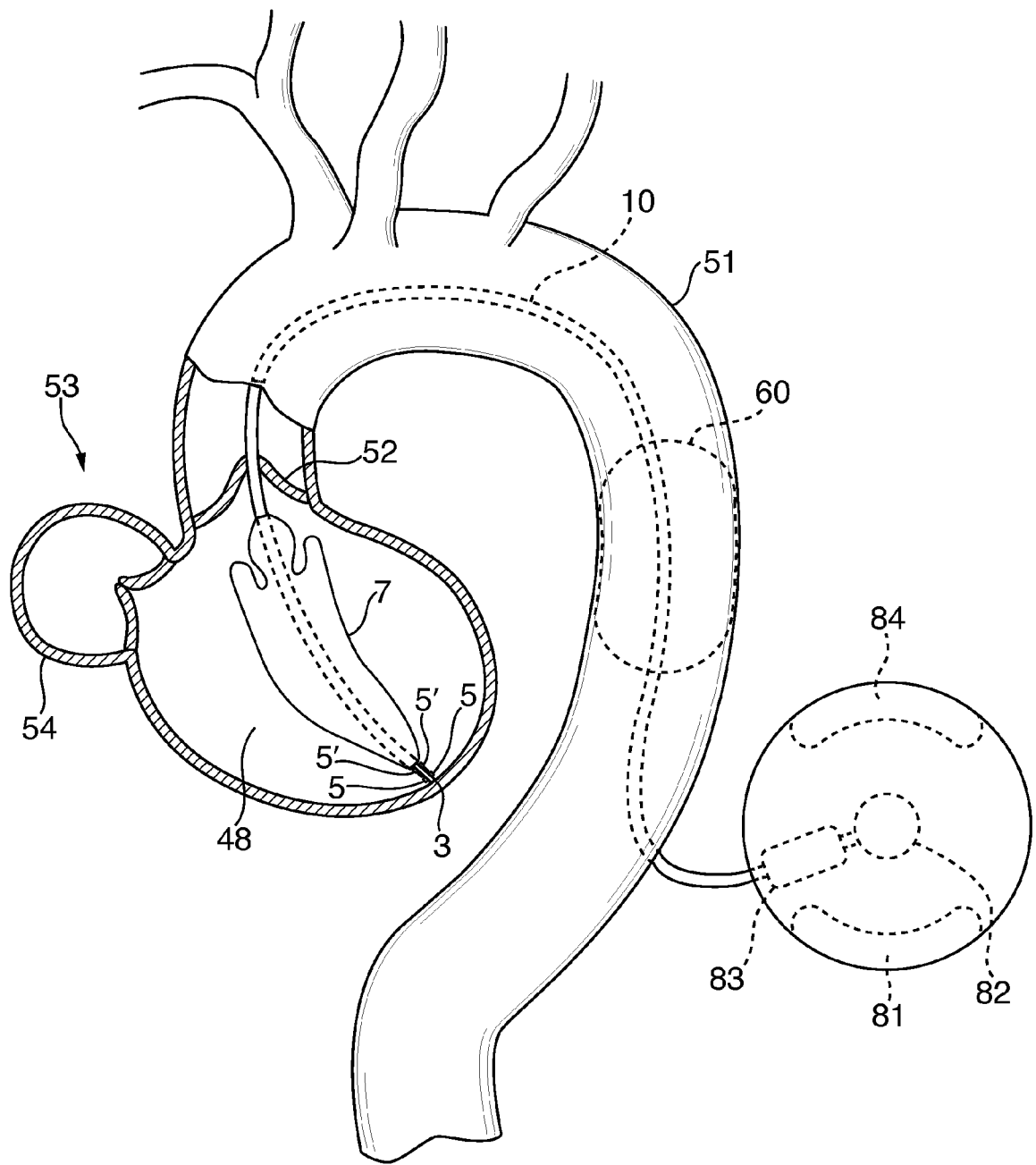
FIG. 8 shows the double balloon pump according to the invention in Type P permanent situations.

Type P is illustrated in FIG. 8. The various parts of the invention device such as the rechargeable battery 81, pump 82, reservoir 83, and pacemaker and stimulus control 84 are in situated within stainless steel box much like an existing pacemaker box. Type P is designed for patients suffering from end stage cardiomyopathy.

Specifically FIG. 8 shows proper positioning of the distal end 3 of the catheter 10 in the left ventricle 48 of a heart 53, only a portion of which is shown in the figures. The balloons 7 and 60 are shown positioned in the left ventricle 48 and the aorta 51, respectively, in their inflated state. The catheter is introduced into the aorta through left mini non-invasive thoraectomy. The I.V.B is directed into the left ventricle and the I.A.B is positioned into the aorta just below the left subclavian artery. The connecting tube is pulled through a side hole in the aortic wall to be connected to the box that is implanted under the pectorals muscle.

As the balloon 7 is brought into the position in the left ventricle, the electrodes 5 and 5' contact the wall of the left ventricle. Upon contacting the wall of the left ventricle, signals indicative of the electrical activity are generated that are input to the processor 34. This provides an indication that the balloon 7 is properly positioned in the left ventricle and the balloon 60 is properly positioned in the descending aorta. Thus, the catheter 10 may be properly positioned without recourse to x-ray images of the catheter.

The main advantages to the double balloon pump are as follows:

1. Efficacy; The ability to double the cardiac output within minutes will be saving ample of lives.
2. Non-invasive: There is no need of any cut of the already compromised myocardium in order to insert it.
3. Minimal anticoagulation is needed and therefore reduced risk of thromboembolus and hemorrhage.
4. No risk of hemolysis as in other devices where small diameter tubes are used.
5. Simple procedure, no surgical skill are needed, no learning curve.
6. Increased coronary flow in addition to increased cardiac output is increasing notably the chances of survival.

The foregoing description of various and preferred embodiments of the present invention has been provided for purposes of illustration only, and it is understood that numerous modifications, variations and alterations may be made without departing from the scope and spirit of the invention as set forth in the following claims.

The invention claimed is:

1. A system for cardiac assist of a heart in a beating stage comprising:
   (a) a double balloon catheter having a proximal end and a distal end, the catheter having at least one lumen;
   (b) an inflatable intra-ventricular balloon mounted on the catheter near the distal end of the catheter, the balloon having a lumen in fluid communication with the lumen of the catheter and being configured for inflation in a ventricle; and
   (c) an intra-aortic balloon mounted on the catheter proximally to the intra-ventricular balloon;
   (d) a control unit comprising:
       (1) a bidirectional pump;
       (2) a fluid reservoir; and
       (3) a processor configured to activate the pump;
   wherein the proximal end of the catheter is configured for attachment to the control unit to form a fluid conduction system in which fluid is configured to be pumped by the pump between the fluid reservoir and the intra-ventricular balloon and the intra-aortic balloon;
   (e) at least one or more electrodes mounted on the catheter near the distal end generating a signal indicative of electrical activity of the heart and wherein the processor is configured to receive the electrical signals to operate the pump to coordinate inflation and deflation of the balloons with the cardiac cycle; wherein the control unit is configured to begin inflating the intraventricular balloon at the end of the slow ejection phase of the beating heart, before closure of either the aortic valve or pulmonic valve in the right ventricle, such that a new pressure wave is created to generate systolic augmentation, and any residual volume of blood left in said ventricle is displaced to achieve a pre-determined intra-ventricular systolic pressure.

2. The system according to claim 1, wherein said slow ejection phase corresponds to the ascending part of the ECG-T wave of the beating heart.

3. The system according to claim 1, wherein said double balloon pump catheter is configured to be introduced into the left ventricle through the femoral artery or into the aorta through a left mini non-invasive thoraectomy.

4. The system according to claim 1, wherein the proximal part of said electrodes are connected to a pacemaker box.

5. The system according to claim 1, wherein the processor is configured to analyze the signal indicative of electrical activity and to identify in the signal one or more phases of the electrical activity of the cardiac cycle.

6. The system according to claim 1, wherein the processor is configured to drive the electrodes to pace the heart.

7. The system according to claim 6 wherein the processor is configured to activate the pump to inflate the intra-ventricular balloon during a predetermined first phase of the cardiac cycle.

8. The system according to claim 7 wherein the predetermined first phase is the end of the slow ejection phase corresponding to the ascending part of the T wave.

9. The system according to claim 5 wherein the processor is configured to activate the pump to deflate the intra-ventricular balloon during a predetermined second phase of the cardiac cycle.

10. The system according to claim 9 wherein the predetermined second phase begins at the peak of systolic augmentation corresponding to the descending part of the T-wave.

11. The system according to claim 1 further comprising a pressure transducer mounted on the catheter near the distal end configured to generating a signal indicative of intra-ventricular blood pressure wherein the processor is configured to receive blood pressure signals.

12. The system according to claim 11 wherein the processor is configured to activate the pump to deliver a volume of the fluid to the intra-ventricular balloon to achieve a predetermined intra-ventricular systolic blood pressure.

13. The system according to claim 11 further comprising a bladder within said control unit which functions as a fluid reservoir, wherein the processor is configured to activate the pump to deliver a volume of the fluid from the intra-ventricular balloon to the bladder.

14. The system according to claim 9 wherein the processor is configured to activate the pump to inflate the intra-aortic balloon during a predetermined third phase of the cardiac cycle.

15. The system according to claim 14 wherein the predetermined third phase of the cardiac cycle is the end of the T wave.

16. The system according to claim 14 wherein the processor is configured to activate the pump to deflate the intra-aortic balloon during a predetermined fourth phase of the cardiac cycle.

17. The system according to claim 16 wherein the predetermined fourth phase of the cardiac cycle is the beginning of the P-wave of the subsequent cycle.

18. A method for cardiac assist of a heart in a beating stage comprising:
   (a) Providing a double balloon catheter having a proximal end and a distal end, the catheter having at least one lumen; and an inflatable balloon mounted on the catheter near the distal end of the catheter, the balloon having a lumen in fluid communication with the lumen of the catheter and being configured for inflation in a ventricle;
   (b) Delivering a first balloon to a ventricle of the heart;
   (c) Delivering the second balloon into the aorta;
   (d) During one or more cardiac cycles, transiently inflating the first balloon to achieve systolic augmentation comprising a new pressure wave which is generated when beginning inflation of said first balloon at the end of the slow ejection phase of the beating heart, and
   (e) inflating the second balloon from the beginning of the diastolic phase and deflating at the end of the diastolic phase, such that any residual volume of blood left in said ventricle is displaced.

19. The method according to claim 18, wherein said slow ejection phase corresponds to the ascending part of the ECG-T wave of the beating heart.

20. The method according to claim 18, wherein the catheter further comprises one or more electrodes mounted on the catheter near the distal end, and the method further comprises generating a signal indicative of electrical activity of the heart.

21. The method according to claim 20, further comprising driving the electrodes to pace the heart.

22. The method according to claim 20, further comprising analyzing the signal indicative of electrical activity and identifying in the signal one or more phases of the electrical activity of the cardiac cycle.

23. The method according to claim 22, further comprising inflating the first balloon during a predetermined first phase of the cardiac cycle.

24. The method according to claim 23, wherein the predetermined first phase is the end of the slow ejection phase corresponding to the ascending part of the T wave.

25. The method according to claim 22, further comprising deflating the first balloon during a predetermined second phase of the cardiac cycle.

26. The method according to claim 25, wherein the predetermined second phase is the peak of the T-wave corresponding to the peak of systolic augmentation and deflation of the first balloon is completed at the end of the T-wave corresponding to the dicrotic notch.

27. The method according to claim 18, wherein the catheter further comprises a pressure transducer mounted on the catheter near the distal end the method further comprises generating a signal indicative of intra-ventricular blood pressure.

28. The method according to claim 27 further comprising delivering a volume of the fluid to the first balloon to achieve a predetermined intra-ventricular systolic blood pressure.

29. The method according to claim 28 further comprising deflating the first balloon to achieve a predetermined intra-ventricular diastolic blood pressure.

30. The method according to claim 18, wherein the ventricle is a left ventricle.

31. The method according to claim 18, further comprising providing a portable rechargeable pump for use in ventricular failure.

* * * * *